United States Patent [19]

Fowler

[11] Patent Number: 6,060,062
[45] Date of Patent: May 9, 2000

[54] LIQUID COMPOSITION FOR THE TOPICAL APPLICATION TO RELIEVE ARTHRITIC PAIN

[76] Inventor: Pearline Fowler, 102-56 184th St., 56D, Hollis, N.Y. 11423

[21] Appl. No.: 09/090,263

[22] Filed: Jun. 4, 1998

Related U.S. Application Data

[60] Provisional application No. 60/050,825, Jun. 26, 1997.

[51] Int. Cl.[7] .............................. A01N 63/00; A01N 65/00
[52] U.S. Cl. ......................................... 424/195.1; 424/93.7
[58] Field of Search ................................ 424/195.1, 93.7

[56] References Cited

U.S. PATENT DOCUMENTS

| | | | |
|---|---|---|---|
| 3,995,030 | 11/1976 | Malachowski | 424/127 |
| 4,271,154 | 6/1981 | Richards | 424/195 |
| 4,582,706 | 4/1986 | Bailey | 424/195 |
| 4,767,626 | 8/1988 | Cheng | 424/195.1 |
| 4,861,797 | 8/1989 | Haas | 514/557 |
| 4,961,933 | 10/1990 | Campos Pino | 424/630 |
| 5,223,257 | 6/1993 | Arora | 424/195.1 |
| 5,223,267 | 6/1993 | Nichols | 424/489 |
| 5,595,743 | 1/1997 | Wu | 424/195.1 |
| 5,691,324 | 11/1997 | Sandyk | 514/159 |
| 5,691,325 | 11/1997 | Sandyk | 514/159 |

*Primary Examiner*—David M. Naff
*Assistant Examiner*—Deborah K. Ware
*Attorney, Agent, or Firm*—Richard C. Litman

[57] ABSTRACT

An analgesic liquid liniment composition for topical application to relieve pain, particularly arthritic pain, is formed containing banana peel extracts, alcohol (preferably wintergreen isopropyl alcohol), parsley, acetylsalicylic acid, and pure gum spirits of turpentine. The composition is prepared by forming a mixture of dried bananas with an alcohol, parsley, acetylsalicylic acid and turpentine, aging and then separating the dried banana peels.

3 Claims, No Drawings

LIQUID COMPOSITION FOR THE TOPICAL APPLICATION TO RELIEVE ARTHRITIC PAIN

CROSS-REFERENCE TO RELATED APPLICATION

This application claims the benefit of U.S. Provisional patent application Ser. No. 60/050,825, filed Jun. 26, 1997.

BACKGROUND OF THE INVENTION

1. Field of the Invention

The present invention relates to a topical composition used to relieve pain and, in particular, pain due to arthritis flare ups.

2. Description of Related Art

From time immemorial man has been plagued by aches and pains, e.g., arthritis. Man has tried various methods and concoctions to try to alleviate these aches and pains. The two major ways man has tried to alleviate aches and pains is to either ingest medicine, or to apply medication topically to the skin in the area where the aches and pains emanate.

The present invention relates to the second method to alleviating aches and pains. Generally, topical analgesic ointments absorb into the skin to deliver the medication to the area where the aches and pains emanate.

The prior art is full of topical ointments used to relieve aches and pains. For example, U.S. Pat. No. 4,582,706, issued Dec. 5, 1984 to Byron H. Bailey shows a liquid topical liniment consisting essentially of a ternary solution of an aliphatic alcohol having up to six carbon atoms, turpentine, camphor, and the soluble materials at room temperature from fresh fig leaves of Ficus Carica.

Another topical composition for relieving aches and pains is shown in U.S. Pat. No. 5,223,257, issued Jun. 29, 1993 to Vasu Arora. The Arora composition consists of approximately equal proportions by volume of wintergreen oil, olive oil and/or oil of Eucalyptus and alcohol.

Yet another ointment for treatment of arthritis is shown in U.S. Pat. No. 4,271,154, issued Jun. 2, 1981 to Levie Richards. The Richards ointment consists of a mixture of white petroleum jelly and the reaction products of lead-free gasoline in combination with dried and ground pods or seeds of the capsicum plants.

Other patents have been issued for topical ointments for pain relief. The following are further examples of such ointments: U.S. Pat. No. 3,995,030, issued Nov. 30, 1976 to Henry Malachowski (Composition and method for treating arthritis); U.S. Pat. No. 4,767,626, issued Aug. 30, 1988 to Theodore Cheng (Remedy for anemia and arthritis); U.S. Pat. No. 4,961,933, issued Oct. 9, 1990 to Longino S. Campos Pino (Preparation for relief of muscle and joint aches); U.S. Pat. No. 5,223,267, issued Jun. 29, 1993 to Larry D. Nichols (Analgesic compositions); and U.S. Pat. No. 5,595,743, issued Jan. 21, 1997 to Wencai Wu (Preparation of herbal medicines by using a multi-enzyme system, herbal medicines prepared and their uses).

None of the above inventions and patents, taken either singly or in combination, is seen to describe the instant invention as claimed.

SUMMARY OF THE INVENTION

A liquid composition used to topically deliver analgesic medication to areas of aches and pains is disclosed. The disclosed composition is particularly effective for treating aches and pains caused by arthritis.

The liquid composition is made from mixing the following ingredients: wintergreen isopropyl alcohol, banana peelings, pure gum spirits of turpentine, parsley leaves and acetylsalicylic acid. The mixture is allowed to age for five or six days at room temperature. The banana peels are then removed from the mixture. The liquid composition is ready for bottling and use.

In order to use the liquid composition, a user massages the liquid in a circular motion into the skin at the site of the ache or pain. The user massages the liquid until the liquid is totally absorbed by the skin. The application of the liniment reduces the acuteness of arthritis aches and pains when acute episodes of aches and pains occur.

Accordingly, it is a principal object of the invention to provide a liquid composition which is topically applied in order to relieve aches and pains which emanate from areas close to the skin.

It is another object of the invention to provide a topically applied liquid composition for pain relief that is pleasant to smell.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

DETAILED DESCRIPTION OF THE PREFERRED EMBODIMENT

The present invention is a liquid composition, generally referred to as "the liniment," for topical application to the skin in order to relieve aches and pain. The liniment is especially effective in alleviating aches and pain caused by arthritis.

The liniment contains extract derived from banana peels, alcohol (preferably wintergreen isopropyl alcohol), pure gum spirits of turpentine, parsley leaves, and acetylsalicylic acid (aspirin).

The following example shows the preferred method for preparing 16–20 fluid ounces (473–591 mL) of the liniment. The first step is to wash 12 bananas and peel them. The banana peels are then dried. The simplest method for drying the banana peels is to allow them to air dry over a period of time. Once the banana peels are dry, they are placed into a mixing container. Next, 16 fluid ounces (473 mL) of isopropyl alcohol are added to the peels in the mixing container. This makes a first admixture. A tablespoon of parsley leaves is added into the container to make a second admixture. Twelve aspirin tablets are then added to the mixture, making a third admixture. The admixture is then mixed thoroughly until the aspirin tablets are completely dissolved. Next, 1 tablespoon of turpentine is added. This is the fourth and final admixture. The admixture is mixed vigorously until the mixture is homogeneous, i.e., there is no liquid separation of the mixture.

The liniment is allowed to age for 5–6 days at room temperature. On the sixth day, the liniment is decanted from the banana peels and is placed in bottles. The liniment is now ready to be massaged into the skin to relieve acute episodes of aches and pains.

While regular isopropyl alcohol may be used, enhanced effects are found when wintergreen isopropyl alcohol is used. Wintergreen isopropyl alcohol contains methyl salicylate in approximately 70% isopropyl alcohol.

Regular aspirin tablets having approximately 325 mg acetylsalicylic acid are preferred. In this situation, 3900 mg of acetylsalicylic acid will be present in a 16–20 ounce (473–591 mL) preparation of the liniment yielding a concentration of approximately 6.6–8.2 mg/mL. Extra strength aspirin, typically about 500 mg per tablet may also be used, yielding approximately 6000 mg per 16–20 ounce preparation. Concentration levels of aspirin using extra strength tablets therefore ranges from approximately 10.2–12.7 mg/mL. Obviously, any level between the low, approximately 6.6 mg/mL, and the high, approximately 12.7 mg/mL, may be made through a combination of various strength tablets.

In use, the ache and pain sufferer merely pours an amount of the liniment onto the site of the pain, or into his or her hands, and rubs the liniment into the skin. Rubbing in a circular motion until the liniment is absorbed by the skin ensures that the liniment enters the skin at the location of the pain. The inventor has found that preparation and use of the compound herein disclosed alleviates or stops arthritis pain for a substantial period of time.

It is to be understood that the present invention is not limited to the sole embodiment described above, but encompasses any and all embodiments within the scope of the following claims

I claim:

1. An analgesic liquid liniment composition for the delivery of a topical anti-arthritic pain relief medicine consisting of:
    a. banana peel extracts;
    b. alcohol;
    c. parsley;
    d. acetylsalicylic acid in a concentration consisting of 6.6 mg/mL to 12.7 mg/mL; and
    e. pure gum spirits of turpentine.

2. The liniment composition according to claim 1, wherein said alcohol is wintergreen isopropyl alcohol containing methyl salicylate.

3. The liniment composition according to claim 1, wherein said banana peel extracts are derived from dried banana peels placed in said composition for at least 5 days, and said dried banana peels are separated from said composition after no more than 6 days.

* * * * *